United States Patent [19]
Kubo et al.

[11] Patent Number: 5,696,580
[45] Date of Patent: Dec. 9, 1997

[54] METHOD OF AND APPARATUS FOR MEASURING ABSORBANCE, COMPONENT CONCENTRATION OR SPECIFIC GRAVITY OF LIQUID SAMPLE

[75] Inventors: Hiroko Kubo; Xu Kexin; Harumi Uenoyama, all of Kyoto, Japan

[73] Assignee: Kyoto Dai-Ichi Kagaku Co., Ltd., Kyoto, Japan

[21] Appl. No.: 434,717

[22] Filed: May 4, 1995

[30]     Foreign Application Priority Data

May 11, 1994    [JP]    Japan .................... 6-123053

[51] Int. Cl.$^6$ .............. G01N 21/00; G01N 21/41
[52] U.S. Cl. .............. 356/72; 356/128; 356/440
[58] Field of Search .................... 356/128–136, 356/436–437, 440, 72

[56]          References Cited

U.S. PATENT DOCUMENTS

| | | | |
|---|---|---|---|
| 4,381,895 | 5/1983 | Hughes et al. | 356/134 |
| 4,730,921 | 3/1988 | Klein et al. | 356/440 |
| 4,834,104 | 5/1989 | Kreinick et al. | 356/136 |
| 5,141,310 | 8/1992 | Boiarski | 356/133 |
| 5,602,647 | 2/1997 | Xu et al. | 356/440 |

*Primary Examiner*—Frank G. Font
*Assistant Examiner*—Jason D. Vierra Eisenberg
*Attorney, Agent, or Firm*—Nikaido Marmelstein Murray & Oram LLP

[57]          ABSTRACT

A measuring beam is incident upon a triangular cell storing a liquid sample, and transmitted light thereof is received by a linear sensor so that both transmitted light intensity and a position of the beam are detected. A refractive index calculating part calculates refractive indices from the position detected by the linear sensor, while an absorbance calculating part calculates absorbance values dependent on component concentration values correcting influence by transmittance change at the triangular cell through the transmitted light intensity values and the refractive indices of the sample calculated at the refractive index calculating part. A component concentration calculating part performs a multivariate analytical operation on the basis of the absorbance values dependent on the component concentration values at a plurality of measuring wavelengths calculated at the absorbance calculating part.

12 Claims, 11 Drawing Sheets

Fig. 2

| SPECIFIC GRAVITY | REFRACTIVE INDEX | SPECIFIC GRAVITY | REFRACTIVE INDEX | SPECIFIC GRAVITY | REFRACTIVE INDEX | SPECIFIC GRAVITY | REFRACTIVE INDEX |
|---|---|---|---|---|---|---|---|
| 1.000 | 1.3330 | 1.010 | 1.3363 | 1.020 | 1.3396 | 1.030 | 1.3430 |
| 1.001 | 1.3333 | 1.011 | 1.3367 | 1.021 | 1.3400 | 1.031 | 1.3433 |
| 1.002 | 1.3337 | 1.012 | 1.3370 | 1.022 | 1.3403 | 1.032 | 1.3436 |
| 1.003 | 1.3340 | 1.013 | 1.3373 | 1.023 | 1.3406 | 1.033 | 1.3440 |
| 1.004 | 1.3343 | 1.014 | 1.3376 | 1.024 | 1.3410 | 1.034 | 1.3443 |
| 1.005 | 1.3347 | 1.015 | 1.3380 | 1.025 | 1.3413 | 1.035 | 1.3446 |
| 1.006 | 1.3350 | 1.016 | 1.3383 | 1.026 | 1.3416 | | |
| 1.007 | 1.3353 | 1.017 | 1.3386 | 1.027 | 1.3420 | | |
| 1.008 | 1.3357 | 1.018 | 1.3390 | 1.028 | 1.3423 | | |
| 1.009 | 1.3360 | 1.019 | 1.3393 | 1.029 | 1.3426 | | |

$\Delta N = 0.33195 \Delta D$ $\Delta D$ ··· SPECIFIC GRAVITY CHANGE FROM 1.000 (20°C)

$\Delta N$ ··· REFRACTIVE INDEX CHANGE FROM 1.333 (20°C)

METHOD OF AND APPARATUS FOR MEASURING ABSORBANCE, COMPONENT CONCENTRATION OR SPECIFIC GRAVITY OF LIQUID SAMPLE

BACKGROUND OF THE INVENTION

1. Field of the Invention

The present invention relates to a method of measuring absorbance values, component concentration values or specific gravity values of various liquid samples such as urine and blood, and an apparatus for measuring the same.

2. Description of the Background Art

Absorbance is measured by the Lambert-Beer's law. The absorption equation of the Lambert-Beer's law at wavelength $\lambda$ in an ideal state is expressed as follows:

$$\log \{Io(\lambda)/I(\lambda)\} = \epsilon(\lambda) \cdot C \cdot L \tag{1}$$

Io ($\lambda$): intensity of light incident upon a cell

I ($\lambda$): intensity of a measuring beam transmitted through the cell $\epsilon(\lambda)$: absorption coefficient of a component (dependent upon the wavelength)

C: component concentration in a solution

L: path length

When the concentration C of a solution and an optical path length L remain unchanged during wavelength scanning, a spectrum can be attained in a form proportionate to an absorption coefficient which is specific to a substance from the equation (1) by measuring Io and I.

Urine specific gravity is an index indicating concentration values of all solutes which are dissolved in the urine, and decided by the urine volume which is adjusted by the kidney and the volume of the solutes which are finally discharged into the urine. The urine specific gravity is generally checked by the following five systems:

(1) A weight method of obtaining the urine specific gravity from the weight ratio of the urine to pure water of the same volume under the same temperature and the same pressure.

(2) An ultrasonic method of obtaining the urine specific gravity by measuring difference between ultrasonic sound velocities caused by a solution density difference.

(3) A test paper method of obtaining the urine specific gravity by measuring ion strength.

(4) A droplet method of obtaining the specific gravity from the rate of sedimentation of urine dropped into a solvent such as oil, for example, which is not mixed with water.

(5) A refractive index method; The refractive index, which is one of a number of optical properties, has strong correlation with purity of a liquid or concentration of a solution. In a solution, it is possible to precisely measure its refractive index. In particular, the refractive index of urine is substantially proportionate to its specific gravity. Thus, the urine specific gravity is obtained from correspondence to the refractive index through a nomogram of the Japan Society of Clinical Pathology shown in FIGS. 2 and 3 prepared by Committee of Standardization of the Japan Society of Clinical Pathology in 1979. In this case, the refractive index is measured by a refractometer.

In a daily test, the refractive index method and the test paper method are generally employed. Test papers which are employed in the test paper method present color tones from blue-green to yellow-green in response to hydrogen ion concentration levels, whereby the urine specific gravity is indicated in seven stages of a 0.005 width in the range of 1.000 to 1.030 through colorimetry of the tones of the test papers. The test paper method is advantageous in a point that the same is hardly influenced by protein and glucose. In the test paper method, however, accuracy of specific gravity presentation is rough at the 0.005 width, while that in the refractive index method is at a 0.001 width. Further, the test paper method is carried out by visual determination, while a measuring apparatus is easy to construct and automatic measurement can be made at a high speed and high accuracy with the refractive index method.

In Japan, dispersion between makers as well as difference with respect to a weight method based on fluctuation in construction ratios of solute components have been corrected to unify the standard in relation to the refractive index method. The following two items have been studied:

(1) Main solutes existing in urine are sodium chloride, urea and the like, which fluctuate in physiological states or morbidity to influence on the urine specific gravity.

(2) In pathological conditions, increase in concentration of protein and glucose and administration of medicine exert further influence on fluctuation of the urine specific gravity.

In consideration of these points, influences exerted by glucose and protein on the urine specific gravity are corrected on the assumption that:

(1) the urine specific gravity is increased by 0.004 per 1% of glucose concentration, and (2) the urine specific gravity is increased by 0.003 per 1% of protein concentration.

Urine specific gravity measurement by the refractive index method is combined with the general test paper method for measuring protein and glucose contained in urine, so that specific gravity obtained through a refractometer is corrected in response to concentration values of glucose and protein obtained by test papers.

There has been proposed a method of obtaining urine specific gravity through the relation between urea concentration and urine specific gravity (refer to Japanese Patent Laying-Open Gazette No. 5-180846 (1993)). According to this method, urea concentration is measured by a urea concentration measuring color identification test device such as a urine test paper for indicating urea concentration in urine by coloration change, and the result is applied to a previously prepared standard color tone table indicating relations between urea concentration values and urine specific gravity values. The standard color tone table is based on the fact that the relation between urea concentration and urine specific gravity is expressed as:

$$\text{urine specific gravity} = \text{urea concentration(mg/dl)} \times 1.43 \times 10^{-5} + 1.008$$

and is formed by equally dividing the range of 1.000 to 1.030 of generally measured urine specific gravity into seven regions per 0.005 and deciding color tones of urea concentration measuring color identification test papers which indicate urea concentrations at each center of the regions.

When a cell of glass or the like is employed as a container for storing a sample in absorption measurement, light is reflected by interfaces between the cell and the air and between the cell and a solution, which influence transmitted light intensity. The reflection between the cell and the air is related to only refractive indices of the air and the cell, and is not dependent on the concentration of the solution. However, the reflection at the interface between the cell and the solution is related to the refractive index of the solution, and varied with the concentration of the solution. Therefore, it is necessary to take the influence exerted on the transmitted light intensity by refraction through transmittance change into consideration.

Considering that the transmitted light intensity is varied through transmittance change resulting from refraction, the transmitted light intensity I is expressed in the following equation (2), from the absorption equation of the Lambert-Beer's law:

$$I = I_o \cdot t(n_o, nc, n) \exp(-\Sigma \alpha i \cdot Ci \cdot L) \qquad (2)$$

αi: absorption coefficient of an i component in the solution (dependent upon the wavelength)
Ci: concentration of the i component in the solution
$t(n_o, nc, n)$: transmittance
  $n_o$: refractive index of the atmosphere
  n: refractive index of the solution
  nc: refractive index of the cell Namely, the refractive indices are varied among the atmosphere, the cell and the solution, and hence the transmittance t as well as the transmitted light intensity I are changed by the wavelength to influence the absorbance, and errors resulting from the transmittance change appear in the results of measurement of the component concentration values.

Various methods of correcting the incident light intensity Io have been devised. For example, there have been carried out (1) a method of making measurement by introducing a reference substance such as water in the same cell, and (2) a method of monitoring a part of light from a light source without passing through the cell. However, errors caused by difference in refractive index resulting from sample concentration are not compensated.

The influence exerted by the transmittance change resulting from refraction on the transmitted light intensity is relatively reduced when the path length L is increased, whereby accuracy of absorption measurement can be improved. If the path length is increased, however, the transmitted light intensity is reduced when a high scattering substance or the like is measured, to deteriorate the signal to noise (S-N) ratio.

In the conventional refractive index method of obtaining urine specific gravity, the refractive indices and the component concentration values are measured by different means respectively, and hence high-priced apparatuses are required with trouble and complicatedness in measurement.

In the method of the aforementioned gazette employing the relation between urea concentration and urine specific gravity, it is impossible to obtain resolution shown in the nomogram of the Japan Society of Clinical Pathology and hence the method is merely applicable to screening in advance of a stage for precisely testing urine specific gravity by employing an apparatus. Upon appearance of an abnormal value, therefore, re-measurement by another method is required. As to coloration states obtained by measuring urea concentration, further, the same or approximate colors appearing on a color identification test device are visually judged and hence individual differences between measurers are included.

SUMMARY OF THE INVENTION

A first object of the present invention is to provide a simple method of and an apparatus for measuring absorbance while compensating for errors resulting from difference between refractive indices of air, a cell and a target substance without increasing the path length, which can also be applied to a high scattering substance.

A second object of the present invention is to provide a method of and an apparatus for obtaining component concentration on the basis of absorbance.

A third object of the present invention is to provide a method of and an apparatus for obtaining component concentration on the basis of absorbance as to not only a urine sample but a general solution sample and further calculating specific gravity through the same.

A fourth object of the present invention is to provide a method of and an apparatus for simply carrying out precise urine specific gravity measurement in high accuracy by simultaneously measuring a refractive index and component concentration of a urine sample by a single measuring device, obtaining urine specific gravity from the relation between the refractive index and specific gravity, and making correction by concentration values of protein and glucose which are correction factors for the urine specific gravity.

In an absorbance measuring method according to the present invention, a liquid sample is stored in a triangular cell having an outgoing plane inclined with respect to an entrance plane for a measuring beam, the measuring beam is introduced perpendicularly to the entrance plane, the measuring beam outgoing from the outgoing plane is received by a linear sensor which can detect both intensity and a position of light, transmitted light intensity is detected every one of a plurality of measuring wavelengths of the measuring beam, the refractive index of the sample is calculated from the position of the measuring beam on the linear sensor, and absorbance is obtained while correcting influence exerted on the transmitted light intensity through transmittance change at the triangular cell with the calculated refractive index, a known atmosphere refractive index and a known cell refractive index.

In a component concentration measuring method according to the present invention, absorbance per measuring wavelength obtained by the aforementioned method is employed for calculating each component concentration by carrying out a multivariate analytical operation.

In a specific gravity measuring method for a liquid sample according to the present invention, density is calculated by adding up respective component concentration values calculated by the above method, for calculating specific gravity on the basis thereof.

In a urine specific gravity measuring method according to the present invention, known data indicating relations between refractive indices and specific gravity values of urine are employed, the refractive index of a urine sample obtained by the above method is applied to the data for obtaining specific gravity of the urine sample, and urine specific gravity increases corresponding to concentration values of glucose and protein are corrected among component concentration values calculated by the aforementioned method.

FIG. 1 shows an apparatus implementing the inventive methods.

Numeral 2 denotes a triangular cell for storing a liquid sample, having an outgoing plane which is inclined with respect to an entrance plane for a measuring beam. This cell 2 is combined with a measuring optical system whose measuring optical path is so set that the measuring beam is perpendicularly incident upon the entrance plane of the triangular cell 2. Numeral 3 denotes a linear sensor provided on a position for receiving the measuring beam outgoing from the outgoing plane of the triangular cell 2, which can detect both intensity and a position of light. Numeral 30 denotes a refractive index calculating part which calculates an amount of displacement of a detecting position at a time of receiving outgoing light from the triangular cell 2 by the linear sensor 3 in case of introducing a sample having an unknown refractive index in the triangular cell 2 with reference to a detecting position at a time of receiving outgoing light from the triangular cell 2 by the linear sensor 3 in case of introducing a liquid having a known refractive index in the triangular cell 2 and calculates the refractive index of the sample corresponding to the amount of displacement through a calibration curve or by calculation. Numeral 31 denotes an absorbance calculating part which calculates absorbance depending on component concentration by correcting influence exerted by transmittance change at the triangular cell 2 through transmitted light intensity at a time of receiving outgoing light from the triangular cell 2 by the linear sensor 3, known incident light intensity, refractive indices of the atmosphere and the cell 2, and the refractive index of the sample calculated by the refractive index calculating part 30. Numeral 32 denotes a component concentration calculating part which calculates respective component concentration values by making multivariate analytical operations on the basis of the absorbance depending on the component concentration at a plurality of measuring wavelengths calculated in the absorbance calculating part 31. Numeral 33 denotes a specific gravity calculating part which calculates density by adding up the respective component concentration values calculated by the component concentration calculating part 32 and calculates specific gravity on the basis thereof. Numeral 35 denotes a urine specific gravity calculating part which employs known data indicating relations between refractive indices and specific gravity values of urine, applies a refractive index of a urine sample obtained in the refractive index calculating part 30 to the data for obtaining the specific gravity of the urine sample, and corrects urine specific gravity increases corresponding to concentration values of glucose and protein among the component concentration values calculated in the component concentration calculating part 32. Numeral 34 denotes an output part such as a recorder or a CRT for outputting the absorbance values, the component concentration values, and the specific gravity of a liquid sample or the urine sample obtained in the respective parts.

The triangular cell employed in the present invention is not restricted to that having a triangular shape. Any triangular cell is employable so far as a pair of glass surfaces transmitting a beam employed for measurement are not parallel to each other but the pair of glass surfaces intersect with each other directly or in extension. In other words, a cell having an outgoing plane which is inclined with respect to an entrance plane for a measuring beam is called a triangular cell.

Operations in the refractive index calculating part 30 and the absorbance calculating part 31 are described.

Calculation of Refractive Index and Absorbance

While a theoretical equation taking influence exerted by the refractive index on transmittance into consideration is indicated in the equation (2), transmittance Io/I is transformed from the equation (2) as follows:

$$Io/I = (1/t)\ exp\ (\Sigma \alpha i \cdot Ci \cdot L) \quad (3)$$

From the equation (3), absorbance A is obtained as follows:

$$\begin{aligned}A &= \log(Io/I) \\ &= \log\{(1/t)\exp(\Sigma \alpha i \cdot Ci \cdot L)\} \\ &= -\log t + \Sigma \alpha i \cdot Ci \cdot L \\ &= An + Ac\end{aligned} \quad (4)$$

Ac: absorbance depending on component concentration Ci

An: absorbance influenced by reflection

From the equation (4), the absorbance Ac depending on the component concentration Ci is obtained as follows:

$$Ac = A - An \quad (5)$$

The absorbance A can be obtained from the equation (4) through measuring values Io and I. The value I is obtained from an output value on a peak position of a waveform transmitted through the cell 2 and caught by the linear sensor 3, as shown in FIG. 4A and 4B in which the triangular cell 2 is employed for simultaneously measuring transmitted light intensity and the refractive index n of a solution. The incident light intensity Io is a value which is specific to the apparatus, and measured in setting of the optical system. From transmittance values at respective interfaces 1, 2, 3 and 4 typically shown in FIG. 5, the value t is as follows:

$$t = t_1 \cdot t_2 \cdot t_3 \cdot t_4 \quad (6)$$

$t_1$: transmittance at the interface 1
$t_2$: transmittance at the interface 2
$t_3$: transmittance at the interface 3
$t_4$: transmittance at the interface 4
$t_1 = t_4$ in the transmittance at the interface between the air and the cell 2, and $t_2 = t_3$ at the interface between the cell 2 and the solution, and hence:

$$t_1 = t_4 = 4n_o \cdot nc/(n_o + nc)^2 \quad (7)$$

$$t_2 = t_3 = 4n_c \cdot n/(nc + n)^2 \quad (8)$$

through Fresnel's formulas. From the equations (7) and (8), the equation (6) is:

$$t = 256 n_o^4 n^2 nc^2/(n_o + nc)^4 (nc + n)^4 \quad (9)$$

Assuming that the refractive index $n_o$ of the air is 1 and a known value decided by the material is employed as the refractive index nc of the cell 2 while a value measured from the apparatus shown in FIG. 4A is employed as the refractive index n of the solution, the value t can be calculated and the absorbance An can be calculated by $An = -\log t$ through the calculated value t.

The principle of measuring the refractive index n of the solution through the apparatus shown in FIG. 4A is now described.

The refractive index calculating part 30 is not adapted to directly obtain the absolute value of a refractive index, but measures difference (defined as an amount of displacement) between a position where an optical axis illuminates a light receiving surface of the linear sensor 3 in FIG. 4A in case of measuring a reference substance (water, for example) and a position where the optical axis illuminates the light receiving surface of the linear sensor 3 in case of measuring a urine sample and converts the amount of displacement to the refractive index.

Referring to FIG. 4A, a measuring beam which is perpendicularly incident upon the entrance plane of the triangular cell 2 is refracted and outgoes into an air layer, to be incident upon the linear sensor 3. The relations between refraction in the cell 2, the solution and the air are as follows:

$$n \cdot \sin \theta_1 = nc \cdot \sin \theta_2 \quad (10)$$

$$nc \cdot \sin \theta_2 = n_o \cdot \sin \theta_3 \quad (11)$$

where $\theta_1$: angle of incidence from the solution to a cell interface $\theta_2$: angle of refraction from a solution side cell interface to a cell layer $\theta_3$: outgoing angle from the cell layer to the air layer $n_o$: refractive index of the air nc: refractive index of the cell n: refractive index of the solution (dependent upon the wavelength).

From the equations (10) and (11):

$$n \cdot \sin \theta_1 = n_o \cdot \sin \theta_3$$

The refractive index n of the solution is as follows:

$$n = n_o \cdot \sin \theta_3 / \sin \theta_1 \quad (12)$$

Since $\sin \theta_1 = \sin \alpha$, the equation (12) is transformed as follows:

$$n = n_o \cdot \sin \theta_3 / \sin \alpha \quad (13)$$

Since the refractive index $n_o$ of the air is 1 and $\alpha$ is the apex angle of the triangular cell 2, the refractive index n of the solution can be obtained by calculation by measuring the angle $\theta_3$ of refraction.

The refractive index is calculated not by measuring the angle $\theta_3$ of refraction but measuring the amount D of displacement of the measuring beam caused by change of the refractive index (change in case of water and in case of a sample solution, for example). The amount D of displacement is obtained by detecting a peak position of a waveform caught by the linear sensor 3 and measuring a distance D to a peak position of a waveform at a time of measuring a sample solution with reference to a peak position Do of a waveform at a time of measuring a reference substance (water, for example). Assuming that an outgoing angle $\theta_3$ from the cell layer to the air layer is changed by $d\theta_3$ at the time of measuring the reference substance and the sample solution, the amount D of displacement is as follows:

$$D = M \cdot d\theta_3$$

where M represents the distance between a light outgoing point of the triangular cell 2 and the linear sensor 3.

On the other hand, $$dn = (n_o \cdot \cos \theta_3 / \sin \alpha) \cdot d\theta_3$$

from the equation (13), and $$dn = D \cdot n_o \cdot \cos \theta_3 / (M \cdot \sin \alpha) \quad (14)$$

from the two equations. The value $\cos \theta_3$ is specific to the apparatus, and measured in setting of the optical system.

According to the equation (14), the difference dn between the refractive indices n and ns of the sample solution and the reference substance is proportional to the amount D of displacement.

$$n = ns + dn$$

Hence, it is possible to obtain the refractive index n of the sample solution only by calculation from measurement of the amount of D of displacement.

A practical method which can obtain a refractive index in high accuracy is that employing a calibration curve. In such a calibration curve method, samples of a certain specific gravity range of 1.000 to 1.030, for example, are employed and a calibration curve equation is guided from data of an amount D of displacement measured by the inventive method and refractive index data independently obtained through a refractometer as to each sample. In measurement of a sample solution, an amount D of displacement is measured by the present invention and a refractive index n is calculated through the calibration curve.

According to the present invention, it is possible to correct influence exerted by refraction on the transmitted light intensity through transmittance change by calculating Ac (=A−An) by the equation (5) through the measured absorbance A and the calculated value An, thereby correctly obtaining the absorbance Ac depending on the component concentration Ci.

Thus, according to the present invention, it is possible to simultaneously measure transmitted light intensity and the refractive index of a liquid sample by employing a triangular cell and a linear sensor and detecting transmitted light intensity of a measuring beam transmitted through the cell and a position of the transmitted light on the linear sensor, thereby correcting influence exerted by refraction on the transmitted light intensity through transmittance change and measuring absorbance in high accuracy.

Further, the transmitted light intensity and the refractive index can be simultaneously measured by a single measuring device, whereby the apparatus structure as well as the operation are simple.

Calculation of Component Concentration

The operation of the component concentration calculating part 32 for calculating component concentration values on the basis of the absorbance Ac depending on component concentration is now described. From the equation (4), the absorbance Ac depending on the component concentration is as follows:

$$Ac = \Sigma \alpha i \cdot Ci \cdot L$$

and an unknown variable is Ci (i=1, 2 ... K: K represents the component number), and hence concentration values of respective components can be calculated by measuring absorbance values at K independent wavelengths and solving simultaneous equations. When data analysis is carried out through a multivariate regression analytical method such as a principal component regression analytical method (PCR method) or a partial least square method (PLS method), the concentration values can be obtained in higher accuracy.

In the multivariate regression analytical method, regression analysis can be made by simultaneously employing a number of absorbance data, whereby quantitative analysis can be made in higher accuracy as compared with single regression analysis. While double regression analysis is most frequently employed, a number of samples are required and quantitative analytical accuracy thereof is extremely reduced when correlation between absorbance values at respective wavelengths is high. On the other hand, the principal component regression analytical method which is a multivariate regression analytical method can intensify multi-wavelength absorbance data to non-correlative principal components and delete unnecessary noise data, whereby high quantitative analytical accuracy can be attained. On the other hand, the partial least square method can also utilize sample concentration data in extraction of principal components, whereby high quantitative analytical accuracy can be attained similarly to the principal component regression analytical method.

According to the present invention, a wavelength having an absolute value of at least 0.5, preferably at least 0.9, of a correlation coefficient between concentration and absorbance in a visible or near-infrared wavelength region of a single component aqueous solution is selected as to each sample component to be measured as a measuring wavelength which is specific to the component, the sample solution is irradiated with visible or near-infrared light, absorbance values are measured as to a plurality of components to be measured at measuring wavelengths selected therefor under the above conditions, and the plurality of sample components are simultaneously subjected to quantitative analysis by a multivariate regression analytical method.

A correlation coefficient Rj as to absorbance A and concentration at a wavelength $\lambda$ is expressed as follows:

$$Rj = \frac{(m-1) \sum_{i=1}^{m} (Aij - \overline{Aj})(Ci - \overline{C})}{\sum_{i=1}^{m} (Aij - \overline{Aj})^2 \cdot \sum_{i=1}^{m} (Ci - \overline{C})^2} \quad (15)$$

where $$\overline{Aj} = \frac{1}{m} \sum_{i=1}^{m} Aij$$

$$\overline{C} = \frac{1}{m} \sum_{i=1}^{m} Ci$$

m: sample number

Aij: absorbance at a wavelength j of a component in an i-th sample

Ci: concentration of the component in the i-th sample

When the sample is prepared from urine, a wavelength region having strong absorption with respect to water is avoided and measuring wavelengths for respective uric components are selected from a wavenumber region of 25000 to 5280 cm$^{-1}$ or 4980 to 4000 cm$^{-1}$ having high transmittance with respect to water.

Preferable measuring wavelengths for the respective components, expressed in wavenumbers, are selected:

from 11380 to 9720 cm$^{-1}$, 9430 to 9400 cm$^{-1}$, 9340 to 9320 cm$^{-1}$, 9260 to 6560 cm$^{-1}$, 6510 to 5540 cm$^{-1}$, 5530 to 5280 cm$^{-1}$, 4980 to 4850 cm$^{-1}$, 4830 to 4480 cm$^{-1}$, 4440 to 4330 cm$^{-1}$ or 4300 to 4010 cm$^{-1}$ for glucose, from 25000 to 7250 cm$^{-1}$, 7220 to 6430 cm$^{-1}$, 6190 to 5690 cm$^{-1}$, 5660 to 5280 cm$^{-1}$ or 4900 to 4080 cm$^{-1}$ for hemoglobin, from 7280 to 6350 cm$^{-1}$, 5910 to 5880 cm$^{-1}$, 5790 to 5740 cm$^{-1}$, 5630 to 5300 cm$^{-1}$, 4900 to 4720 cm$^{-1}$, 4670 to 4280 cm$^{-1}$ or 4230 to 4070 cm$^{-1}$ for albumin, from 8490 to 6360 cm$^{-1}$, 6040 to 5610 cm$^{-1}$, 5430 to 5300 cm$^{-1}$, 4900 to 4760 cm$^{-1}$, 4680 to 4510 cm$^{-1}$ or 4470 to 4320 cm$^{-1}$ for lithium acetoacetate, from 7270 to 6520 cm$^{-1}$, 6430 to 5290 cm$^{-1}$, 4950 to 4860 cm$^{-1}$ or 4810 to 4090 cm$^{-1}$ for ascorbic acid, from 9370 to 5870 cm$^{-1}$, 5810 to 5280 cm$^{-1}$, 4980 to 4730 cm$^{-1}$, 4690 to 4320 cm$^{-1}$ or 4290 to 4090 cm$^{-1}$ for creatinine, from 7640 to 5280 cm$^{-1}$ or 4980 to 4080 cm$^{-1}$ for sodium chloride, and from 8680 to 5300 cm$^{-1}$, 4980 to 4210 cm$^{-1}$ or 4160 to 4100 cm$^{-1}$ for sodium nitrite.

Thus, absorbance of a liquid sample can be correctly measured every measuring wavelength according to the present invention, whereby each component concentration can be calculated in high accuracy by a multivariate analytical operation.

Calculation of Specific Gravity

The operation of the specific gravity calculating part 33 is described. The specific gravity calculating part 33 calculates specific gravity from all component concentration values in the sample solution obtained in the component concentration calculating part 32. Density $\rho$ is defined as follows:

$$\rho = m/V \quad (15)$$

m: weight of all components

V: volume of sample solution

Assuming that mi represents the weight of each component, volume concentration Ci of each component is expressed as follows:

$$Ci = mi/V \quad (16)$$

$m = \Sigma mi$, and hence:

$$\rho = m/V \quad (17)$$
$$= \Sigma mi/V$$
$$= \Sigma Ci$$

from the equations (15) and (16). The specific gravity can be obtained from the density obtained in the equation (17) and that of water (constant). Thus, the specific gravity can be obtained from the component concentration values by calculation without measuring the weight of each component.

This method of obtaining specific gravity of a sample solution by calculation is applicable to a urine sample as a matter of course, while the same is also generally applicable to other solution samples.

Measurement of Urine Specific Gravity

A method of calculating the refractive index of a urine sample by the refractive index calculating part 30 and calculating urine specific gravity in the urine specific gravity calculating part 35 is now described. This method alone is specific to a urine sample, and not applicable to a solution sample other than urine.

The urine specific gravity calculating part 35 employs a refractive index obtained in the refractive index calculating part 30, and calculates specific gravity from nomograms shown in FIGS. 2 and 3.

Further, it corrects the specific gravity value obtained from the nomograms shown in FIGS. 2 and 3 on the basis of the fact that:

glucose... urine specific gravity is increased by 0.004 per 1% concentration protein... urine specific gravity is increased by 0.003 per 1% concentration by employing concentration values of glucose and protein among component concentration values calculated while correcting influence exerted by refraction on transmitted light intensity through transmittance change by the absorbance calculating part 31 and the component concentration calculating part 32.

Namely, it is possible to carry out simple and precise urine specific gravity measurement by a single method and a single apparatus by obtaining concentration values of glucose and protein which are correction factors for the specific gravity from absorbance measurement by simultaneous measurement of a refractive index and absorbance values and correcting the urine specific gravity on the basis thereof.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a table of a nomogram proposed by the Japan Society of Clinical Pathology indicating standard references of refractive indices and specific gravity values of urine;

DESCRIPTION OF THE PREFERRED EMBODIMENTS

Figure 1:
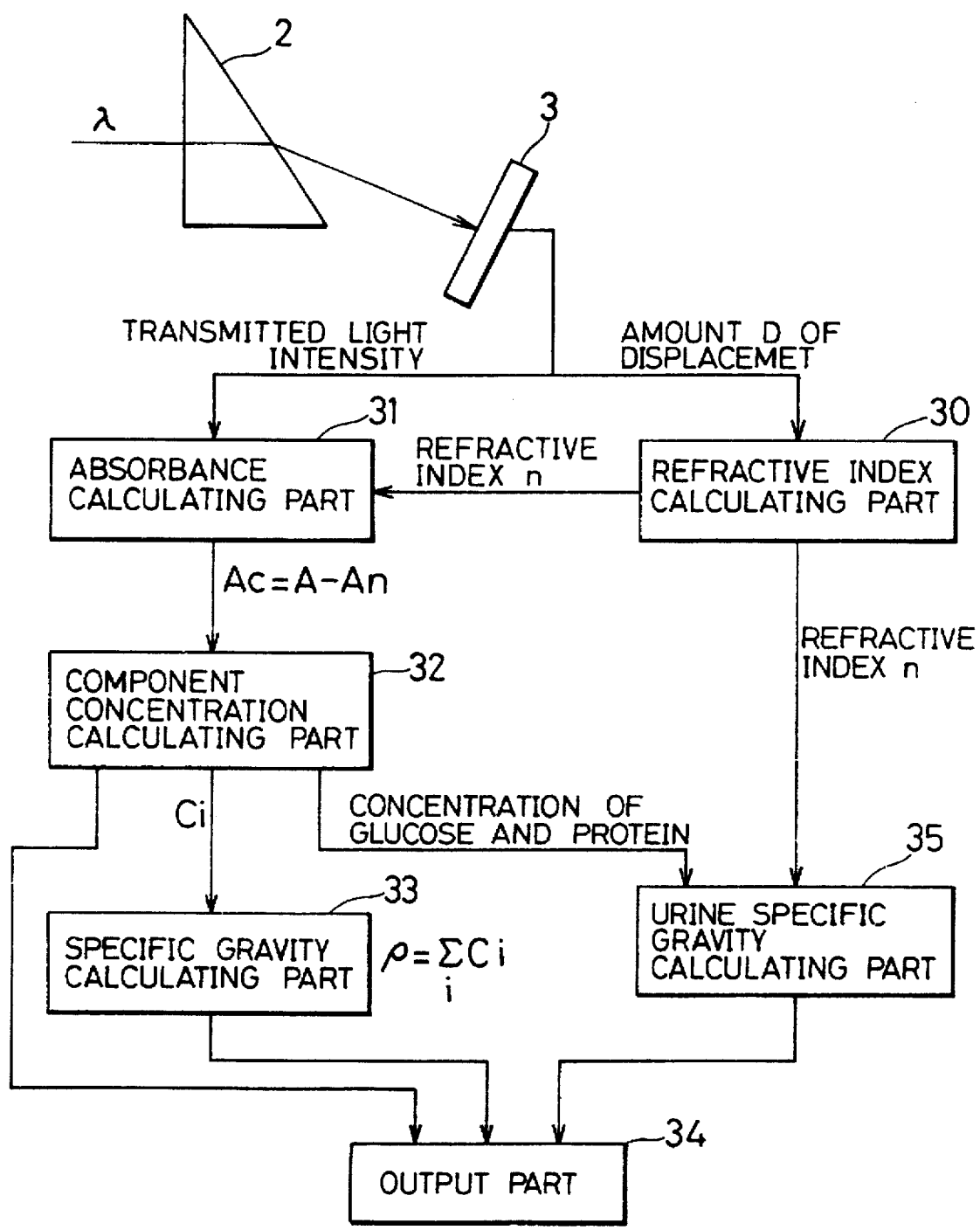
FIG. 1 is a block diagram showing an apparatus according to the present invention.
Figure 3:
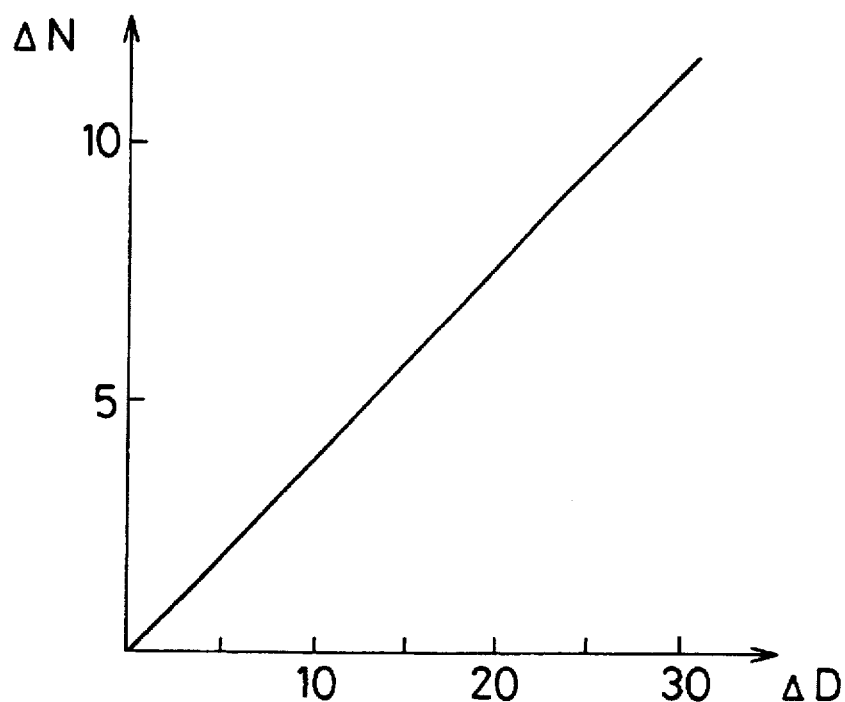
FIG. 3 is a graph of the nomogram.
Figure 4A:
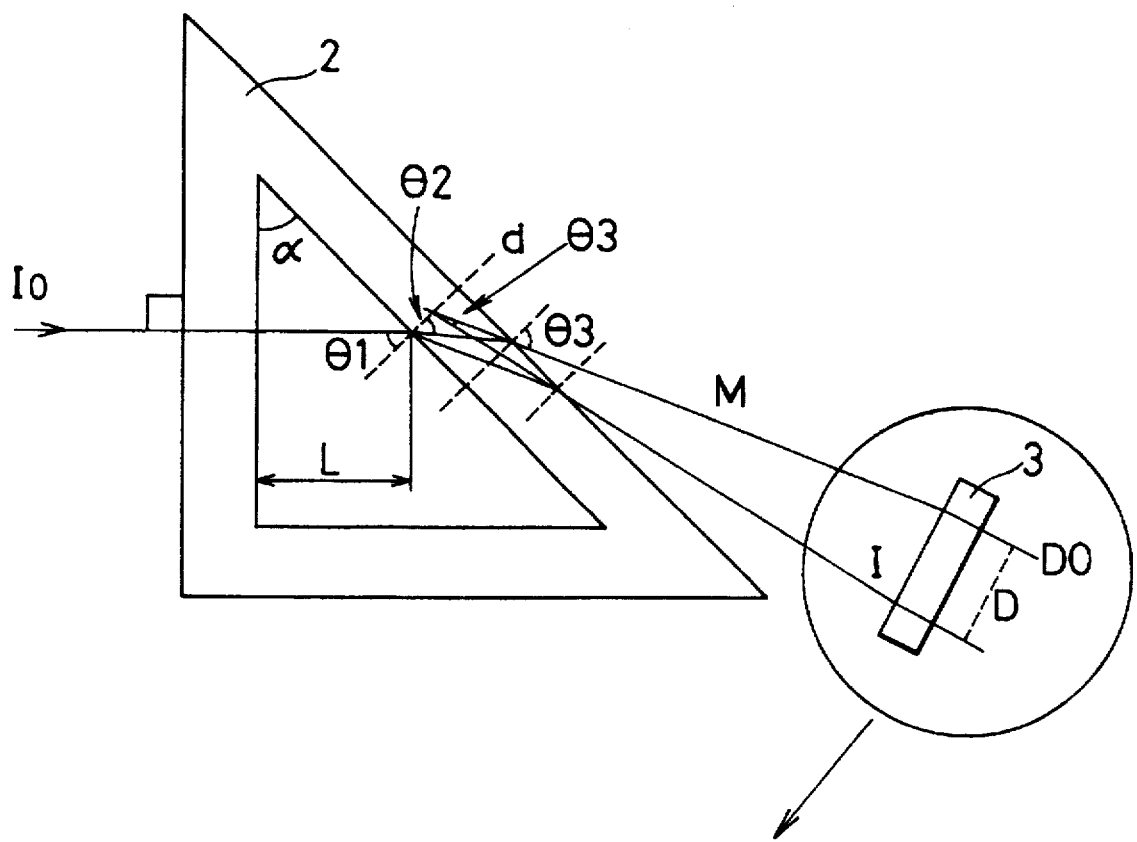
FIGS. 4A and 4B are a plan view showing a cell and a linear sensor and a diagram showing the linear sensor and intensity of cell transmission light received by the linear sensor respectively, for illustrating a principle of simultaneous measurement of transmission light intensity and a refractive index through a triangular cell in the present invention.
Figure 4B:
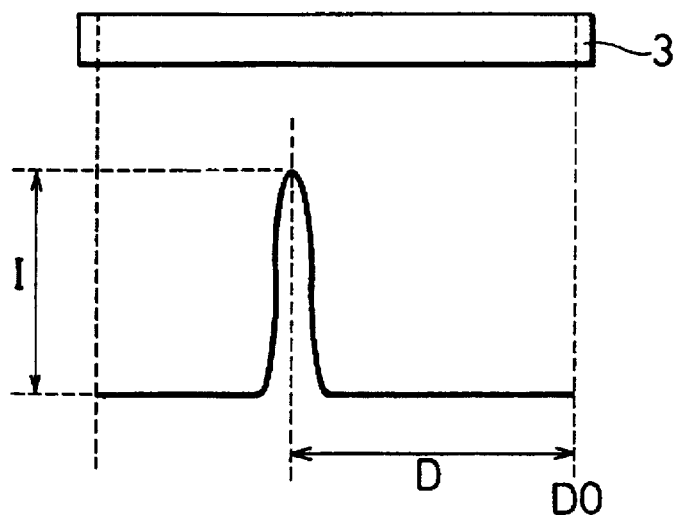
Figure 5:
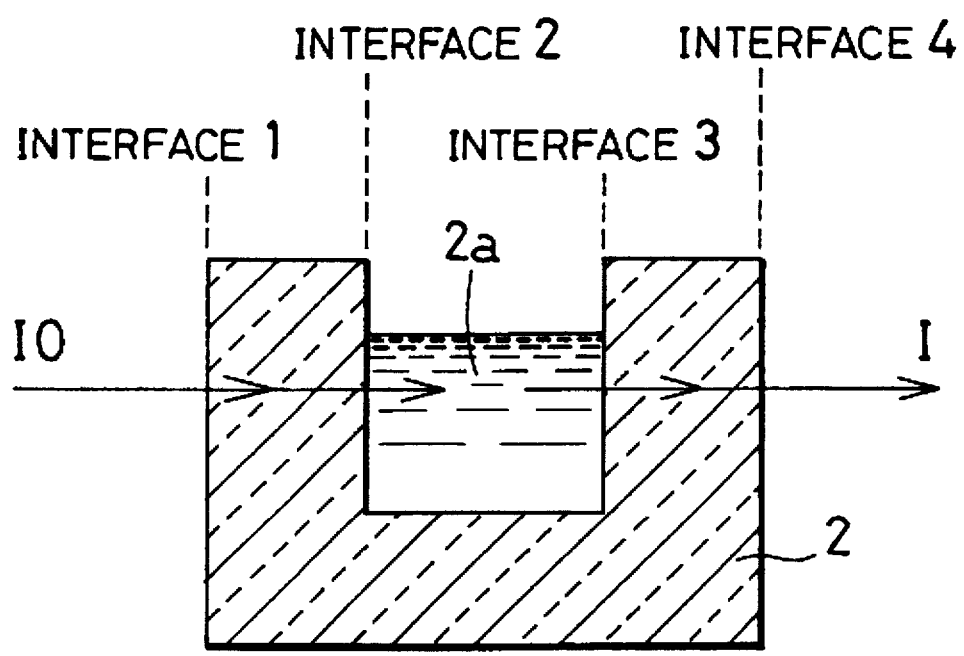
FIG. 5 is a sectional view of a cell, typically showing transmission of light which is applied to the cell and transmitted through respective interfaces.
Figure 6:
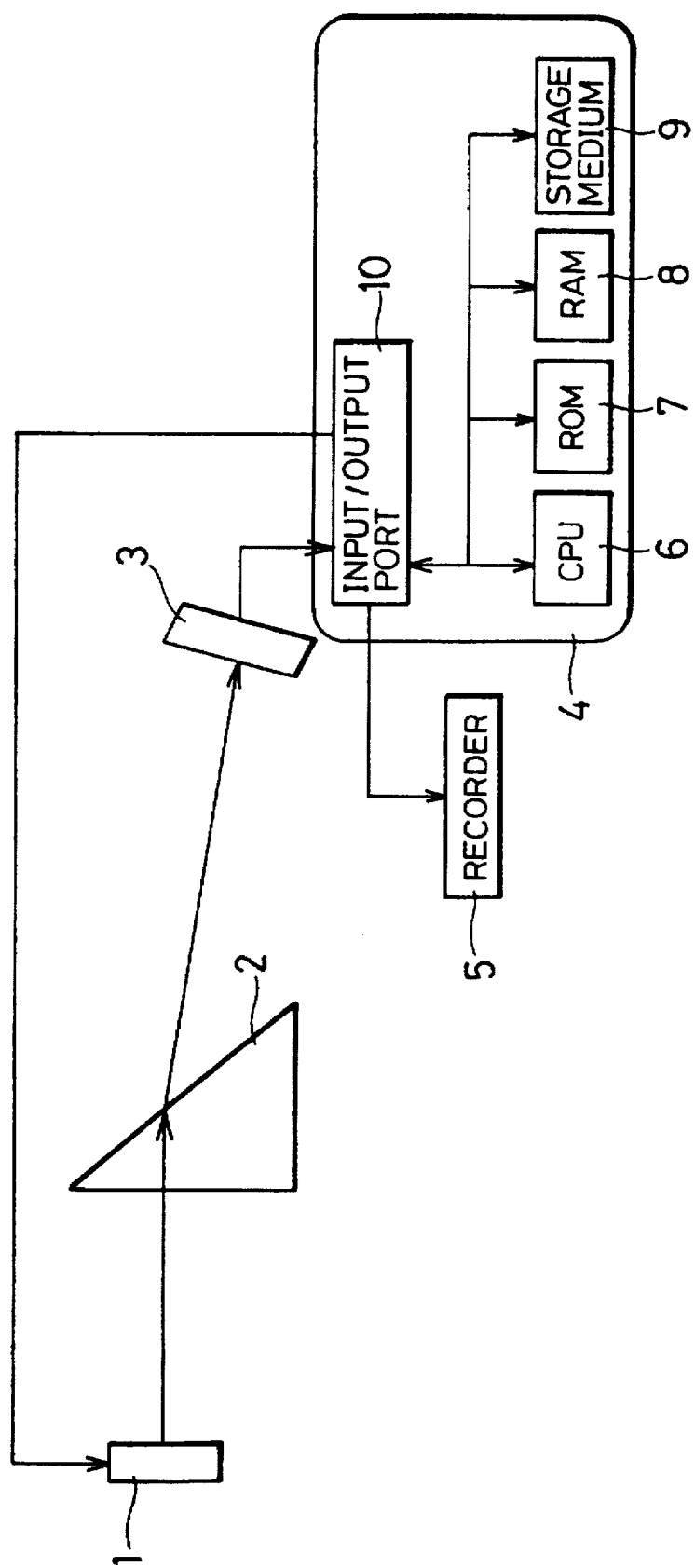
FIG. 6 is a schematic block diagram showing the overall structure of a first embodiment of the present invention.

FIG. 6 illustrates a first embodiment of the present invention. A light source 1, which can selectively emit measuring beams of a plurality of wavelengths, is formed by a laser diode (LD) array, a variable wavelength laser, or a combination of a light source emitting multiple wavelengths and a spectroscope, for example. The light source 1 and a triangular cell 2 are so arranged that a measuring beam from the light source 1 is perpendicularly incident upon an entrance plane of the cell 2. The measuring beam which is transmitted through the cell 2 and refracted is received by a linear sensor 3. The linear sensor 3, which can convert both of the intensity and the position of incident light to electric signals and output the same, can be formed by a photodiode array or a CCD sensor. A data processing part 4 includes an input/output port 10 which separates the electric signals from the linear sensor 3 into signals for respective wavelengths and A–D (analog-to-digital) converts the same into digital signals, a CPU 6, a ROM 7, a RAM 8 and a storage medium 9 such as a magnetic memory device. Numeral 5 denotes a recorder serving as an output part. The data processing part 4 implements the refractive index calculating part 30, the absorbance calculating part 31, the composition concentration calculating part 32, the specific gravity calculating part 33 and the urine specific gravity calculating part 35 appearing in FIG. 1.

Figure 7:
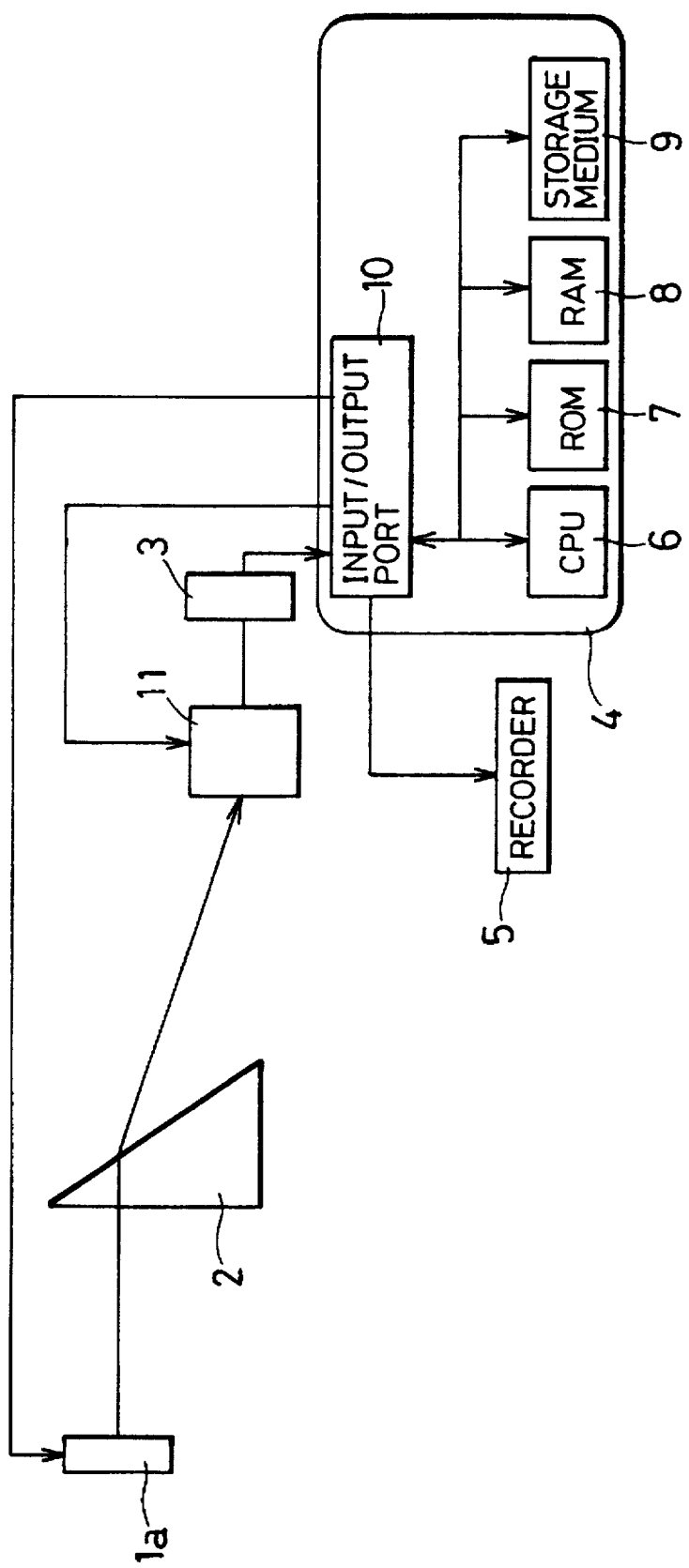
FIG. 7 is a schematic block diagram showing the overall structure of a second embodiment of the present invention.

FIG. 7 shows a second embodiment of the present invention. A light source 1a such as a halogen lamp is adapted to simultaneously emit a plurality of wavelengths. A measuring beam which is transmitted through a cell 2 is received by a linear sensor 3 through a spectroscope 11. The spectroscope 11 is not a diffraction grating, but a filter rotor which comprises a plurality of interference filters for separating light into its spectral components by switching filters onto an optical path. While the incident light of the measuring beam in FIG. 6 is that having a selected wavelength, the incident light in FIG. 7 includes a plurality of wavelengths and transmitted light is separated into spectral components so that a wavelength is selected. A data processing part 4 is identical in structure to that in FIG. 6.

Figure 8:
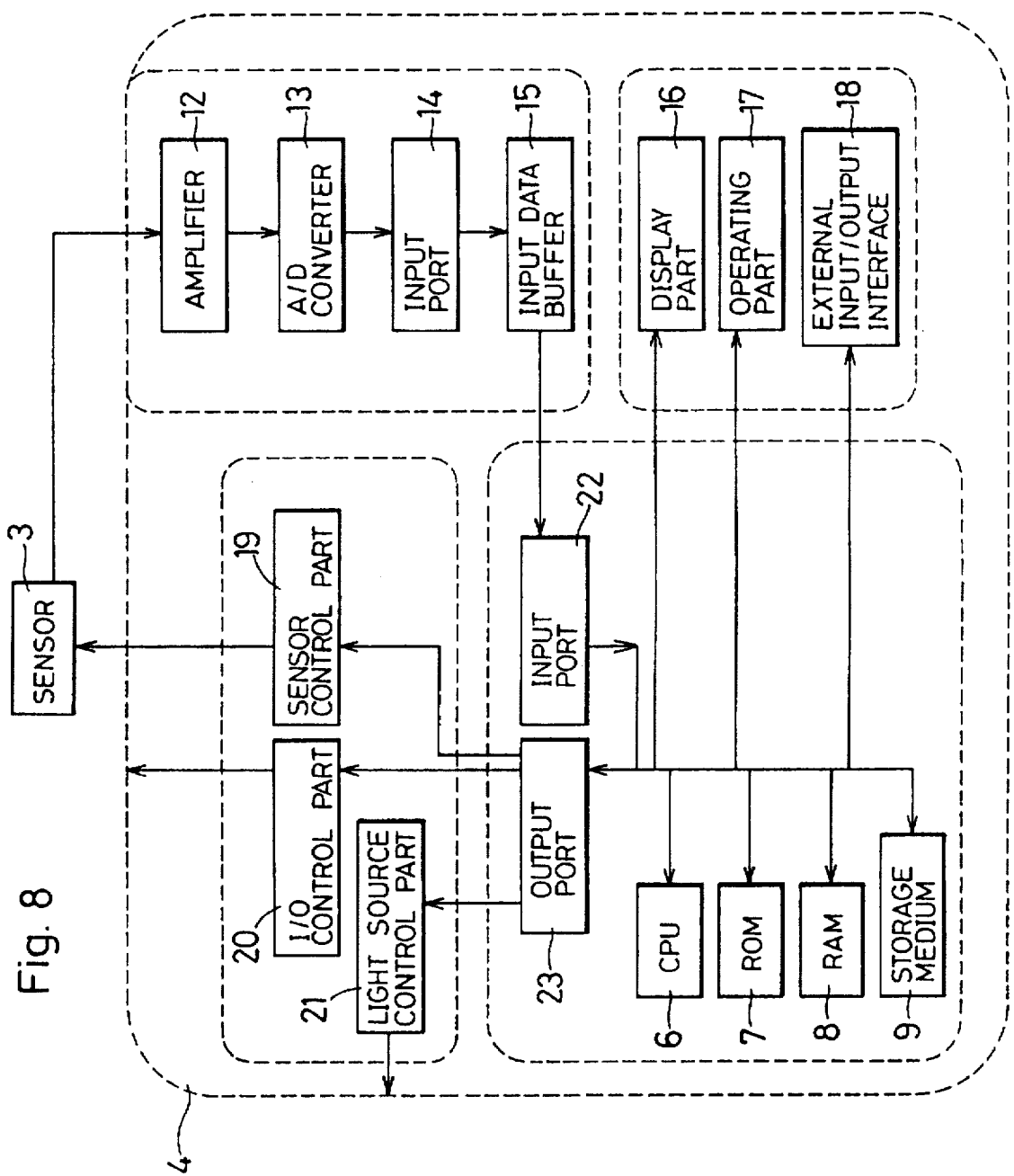
FIG. 8 is a block diagram showing a data processing part in each embodiment.

FIG. 8 more concretely shows the data processing part 4 shown in each of FIGS. 6 and 7. The input/output port 10 shown in FIG. 6 or 7 includes an amplifier 12 for amplifying the output of the sensor 3, an A–D converter 13 for conversion to a digital signal, an input port 14, an input data buffer 15, an input port 22, an output port 23, a sensor control part 19, an I/O control part 20 and a light source control part 21. The data processing part 4 further comprises a display part 16, an operating part 17, and an external input/output interface 18.

A flow of processing for obtaining component concentration through the embodiment shown in FIG. 6 or 7 is now described with reference to a flow chart shown in FIG. 9.

When a power source for the data processing part 4 is turned on, a power source for the overall control part is turned on to initialize a microcomputer part provided in the data processing part 4 as well as the CPU 6 and the RAM 8. After a microcomputer operation is enabled, initial value data related to measurement and an apparatus operation are input from the storage medium 9 and written in the RAM 8. The apparatus is initialized on the basis of these data, to wait for an instruction for starting of measurement.

A sample is injected into the triangular cell 2 and set in a prescribed position. A start button is pushed to start a measuring operation. A measuring beam from the light source 1 or 1a is perpendicularly incident upon the entrance plane of the triangular cell 2, to be transmitted through the triangular cell 2 and received by the linear sensor 3. The linear sensor 3 converts a light signal to an electric signal. The data processing part 4 A–D converts the electric signal with respect to one measuring wavelength from the linear sensor 3 and incorporates the same as a digital signal. Transmitted light intensity I and an amount D of displacement are detected from the electric signal from the linear sensor 3.

The measuring beam is switched to a next measuring wavelength. The measuring wavelength is switched by switching a lighting LD element at the light source 1, switching the wavelength of a variable wavelength laser or scanning a spectroscope in the embodiment shown in FIG. 6 or by switching a filter in the spectroscope 11 in the embodiment shown in FIG. 7. An electric signal received from the linear sensor 3 at the switched measuring wavelength is similarly A–D converted and incorporated. Thus, intensity I of light transmitted through the cell 2 and an amount D of displacement are detected every measuring wavelength and incorporated.

When incorporation of electric signals from the linear sensor 3 at planned wavelengths is completed, refractive indices are obtained from the amounts D of displacement, and the transmitted light intensity values I are corrected through the refractive indices for obtaining absorbance. Absorbance values at a plurality of measuring wavelengths are employed to carry out multivariate analytical operations for obtaining component concentration values. The results are output to the recorder 5 and the like. Finally the power source for the data processing part 4 is turned off to complete the measurement.

An operation for obtaining specific gravity from respective component concentration values through the embodiment shown in FIG. 6 or 7 is described with reference to a flow chart of FIG. 10.

Figure 9:
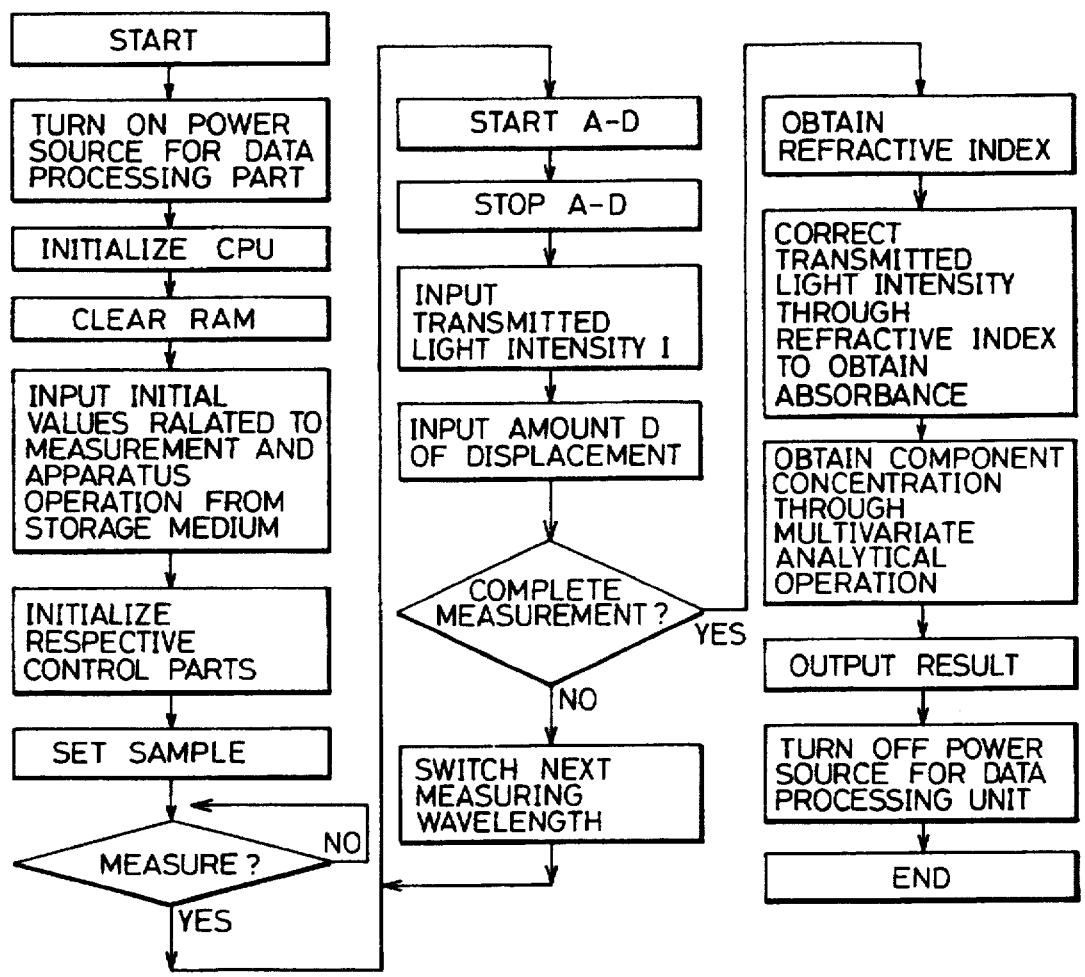
FIG. 9 is a flow chart showing an operation for obtaining component composition.

The power source for the data processing part 4 is turned on, a sample is set to start measurement and data incorporation is completed through a procedure identical to that of FIG. 9. Referring to FIG. 10, refractive indices are obtained, transmitted light intensity values are corrected through the refractive indices to obtain absorbance values, and component concentration values are obtained from the absorbance values by multivariate analytical operations. When the respective component concentration values are obtained, density is obtained by the sum of all component concentration values, thereby obtaining the specific gravity of the sample not only in a urine sample but with respect to a general solution sample.

An operation of obtaining the specific gravity of a urine sample through the embodiment shown in FIG. 6 or 7 is described with reference to a flow chart shown in FIG. 11.

Figure 10:
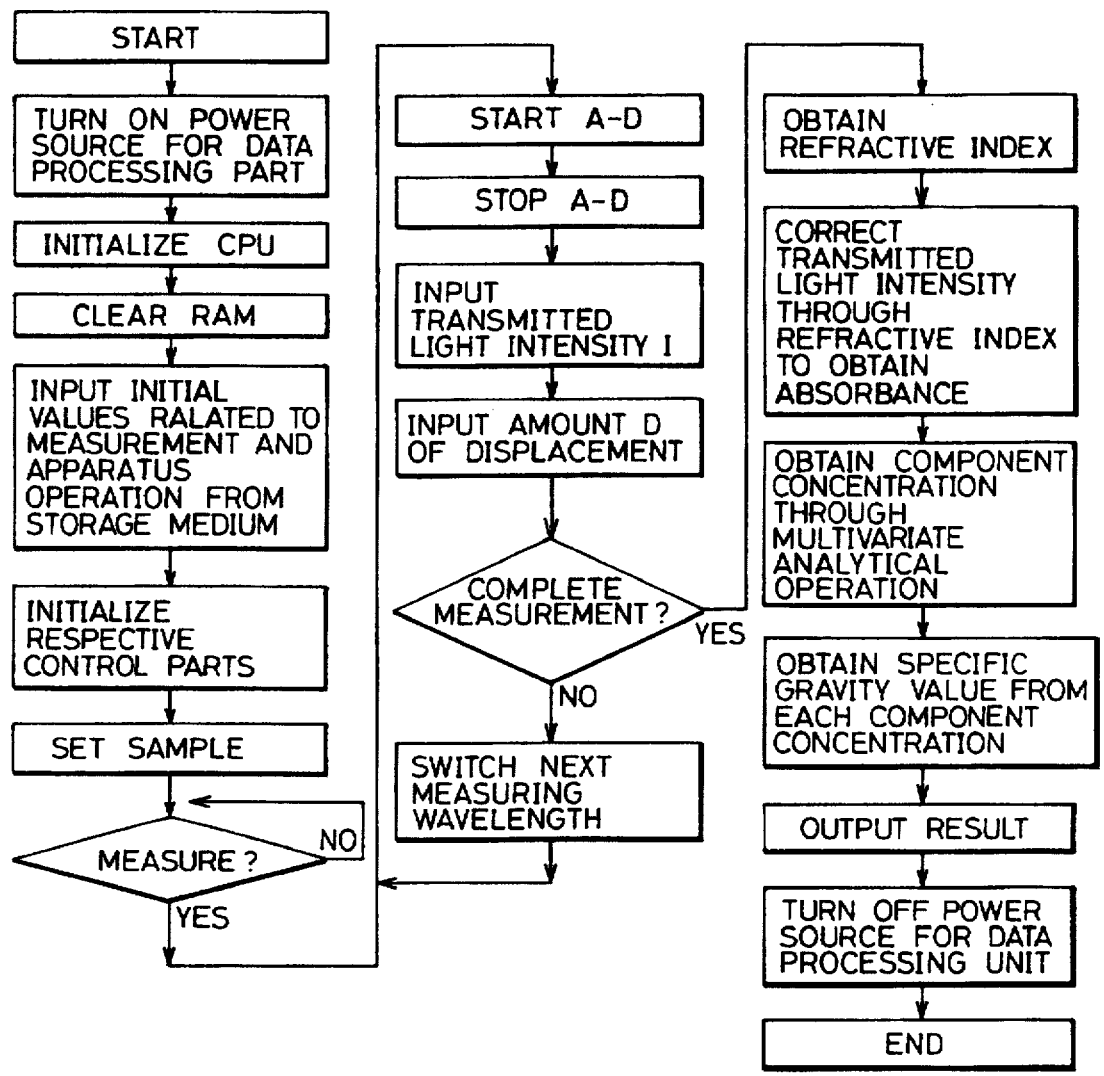
FIG. 10 is a flow chart showing an operation for obtaining a specific gravity value from component composition.

Also in this case, the power source for the data processing part 4 is turned on, the sample is set, wavelengths of the light source 1 or 1a is switched, and electric signals received from the linear sensor 3 at respective wavelengths are converted to digital values and incorporated, similarly to the operations shown in FIGS. 9 and 10.

Figure 11:
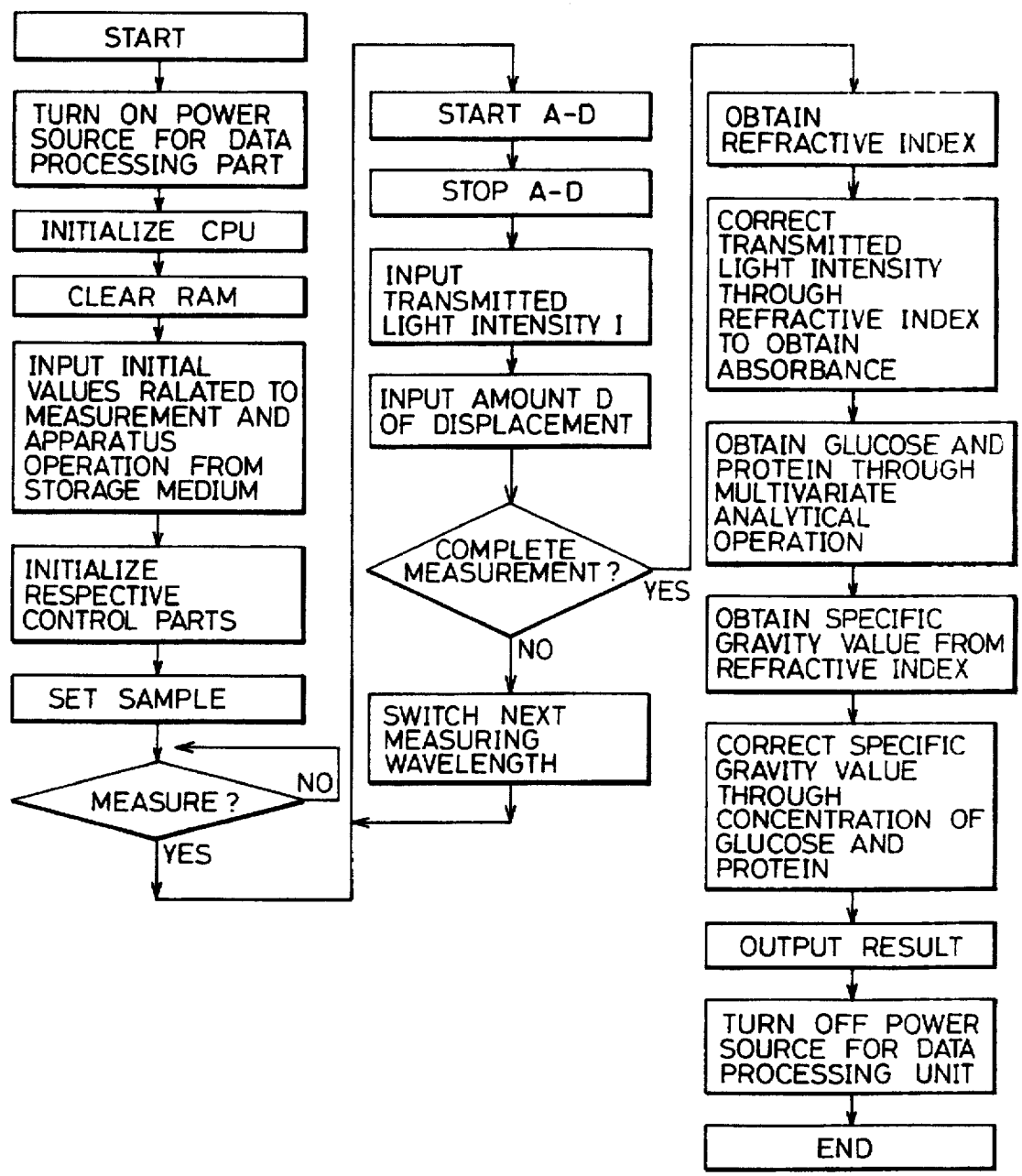
FIG. 11 is a flow chart showing an operation for obtaining a specific gravity value of a urine sample.

Referring to FIG. 11, refractive indices are obtained, and transmitted light intensity values are corrected to obtain absorbance values, for obtaining concentration values of glucose and protein on the basis thereof by multivariate analytical operations. On the other hand, known data showing relations between refractive indices and specific gravity values are employed and the refractive indices obtained by the measurement are applied thereto to obtain the specific gravity value of the sample. On the other hand, the specific gravity value is corrected by the concentration values of glucose and protein obtained by the multivariate analytical operations, and the result is output.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A measuring method comprising the steps of:

storing a liquid sample in a triangular cell having an outgoing plane being inclined with respect to an entrance plane for a measuring beam;

introducing said measuring beam in a direction perpendicular to said entrance plane;

receiving said measuring beam outgoing from said outgoing plane by a linear sensor detecting both intensity and a position of light;

detecting transmitted light intensity of said measuring beam;

calculating a refractive index n of said sample from the position of said measuring beam on said linear sensor; and obtaining absorbance Ac with correction of influence being exerted on said transmitted light intensity through transmittance change in said triangular cell through said calculated refractive index, a known atmosphere refractive index and a known cell refractive index.

2. The measuring method in accordance with claim 1, wherein absorbance A is obtained through the following equation:

$$A = \log(I_o/I)$$

where $I_o$ represents said incident light intensity of said measuring beam, and I represents said transmitted light intensity being transmitted through said triangular cell and received by said linear sensor, said refractive index n of said sample is obtained through the following equation:

$$n = n_s + D \cdot n_o \cdot \cos\theta_3 / M \cdot \sin\alpha$$

where $n_o$ represents a refractive index of a reference substance, ns represents a refractive index of air, M represents the distance between a light outgoing point of said triangular sensor and said linear sensor, $\theta_3$ represents an outgoing angle from a cell layer of said triangular cell to an air layer, and $\alpha$ represents an apex angle of said triangular cell, M, $\theta_3$ and $\alpha$ being values specific to an apparatus, where D represents an amount of displacement from a peak position of a waveform at a time of measuring said reference substance to that of a waveform at a time of measuring said sample, for obtaining absorbance An being influenced by reflection through said refractive index n of said sample solution as follows:

$$An = -\log t$$

where t represents a transmittance of said triangular cell resulting from refraction through Fresnel's formulas using said refractive index n, and said absorbance Ac dependent upon component concentration Ci is obtained as follows:

$$Ac = A - An.$$

3. The measuring method in accordance with claim 1, wherein absorbance A is obtained through the following equation:

$$A = \log(I_o/I)$$

where $I_o$ represents said incident light intensity of said measuring beam, and I represents said transmitted light intensity being transmitted through said triangular cell and received by said linear sensor, a calibration curve showing the relation between an amount D of displacement from a peak position of a waveform at a time of measuring a reference substance to that of a waveform at a time of measuring a standard sample and a separately measured refractive index of said standard sample is prepared, said refractive index n of said sample is calculated from an amount D of displacement from a peak position of a waveform at a time of measuring said reference substance to that of a waveform at a time of measuring said sample is measured through said calibration curve, absorbance An being influenced by reflection is obtained as:

$$An = -\log t$$

where t represents a transmittance of said triangular cell resulting from refraction through Fresnel's formulas using said refractive index n of said sample solution, and said absorbance Ac dependent on component concentration Ci is obtained as follows:

$$Ac = A - An.$$

4. The measuring method in accordance with claim 1, wherein detection of said transmitted light intensity by said linear sensor and detection of said position of said measuring beam on said linear sensor are carried out every one of a plurality of measuring wavelengths of said measuring beam, and said absorbance Ac with correction influence being exerted on said transmitted light intensity through transmittance change in said triangular cell is calculated every said measuring wavelength, and multivariate analytical operations are carried out for calculating respective component concentration values of said sample.

5. The measuring method in accordance with claim 4, wherein density is calculated by adding up calculated respective said component concentration values, for calculating specific gravity on the basis thereof.

6. The measuring method in accordance with claim 4, wherein said sample is urine, known data showing relations between refractive indices and specific gravity values of urine are employed so that sample refractive index n obtained from said position of said measuring beam is applied to said data for obtaining specific gravity of said urine sample, and urine specific gravity increases corresponding to concentration values of glucose and protein among said component concentration values are corrected.

7. A measuring apparatus comprising:

a triangular cell for storing a liquid sample, having an outgoing plane being inclined with respect to an entrance plane for a measuring beam;

a measuring optical system having a measuring optical path being so set as to introduce said measuring beam perpendicularly to said entrance plane of said triangular cell;

a linear sensor being provided on a position for receiving said measuring beam outgoing from said outgoing plane of said triangular cell and said linear sensor detecting both intensity and a position of light;

a refractive index calculating part for detecting an amount of displacement of a detected position at a time of receiving said measuring beam from said triangular cell by said linear sensor in case of measurement with introduction of a sample having an unknown refractive index in said triangular cell with reference to a detected position at a time of receiving said measuring beam from said triangular cell by said linear sensor in case of measurement with introduction of a liquid having a known refractive index in said triangular cell, and calculating a refractive index of said sample corresponding to said amount of displacement through a calibration curve or by calculation; and an absorbance calculating part for calculating absorbance Ac being dependent on component concentration with correction of influence by transmittance change at said triangular cell through transmitted light intensity at a time of receiving said measuring beam from said triangular cell by said linear sensor, known incident light intensity, refractive indices of the atmosphere and said cell, and said refractive index of said sample being calculated in said refractive index calculating part.

8. The measuring apparatus in accordance with claim 7, further comprising a component concentration calculating part carrying out multivariate analytical operations on the basis of absorbance values depending on component concentration values at a plurality of measuring wavelengths being calculated in said absorbance calculating part for calculating respective component concentration values.

9. The measuring apparatus in accordance with claim 8, further comprising a specific gravity calculating part calculating density by adding up respective said component concentration values being calculated by said component concentration calculating part for calculating specific gravity on the basis thereof.

10. The measuring apparatus in accordance with claim 8, further comprising a urine specific gravity calculating part employing known data indicating relations between refractive indices and specific gravity values of urine, obtaining specific gravity of a urine sample by applying said sample refractive index obtained in said refractive index calculating part to said data, and correcting urine specific gravity increases corresponding to concentration values of glucose and protein among said component concentration values being calculated in said component concentration calculating part.

11. A measuring method comprising the steps of:

storing a liquid sample in a triangular cell having an outgoing plane being inclined with respect to an entrance plane for a measuring beam;

introducing said measuring beam to said entrance plane;

receiving said measuring beam outgoing from said outgoing plane by a linear sensor detecting both intensity and a position of light;

detecting transmitted light intensity of said measuring beam;

calculating a refractive index n of said sample from the position of said measuring beam on said linear sensor; and obtaining absorbance Ac with correction of influence being exerted on said transmitted light intensity through transmittance change in said triangular cell through said calculated refractive index, a known atmosphere refractive index and a known cell refractive index.

12. A measuring apparatus comprising:

a triangular cell for storing a liquid sample, having an outgoing plane being inclined with respect to an entrance plane for a measuring beam;

a measuring optical system having a measuring optical path being so set as to introduce said measuring beam to said entrance plane of said triangular cell;

a linear sensor being provided in a position for receiving said measuring beam outgoing from said outgoing plane of said triangular cell and said linear sensor detecting both intensity and a position of light;

a refractive index calculating part for detecting an amount of displacement of a detected position at a time of receiving said measuring beam from said triangular cell by said linear sensor in case of measurement with introduction of a sample having an unknown refractive index in said triangular cell with reference to a detected position at a time of receiving said measuring beam from said triangular cell by said linear sensor in case of measurement with introduction of a liquid having a known refractive index in said triangular cell, and calculating a refractive index of said sample corresponding to said amount of displacement through a calibration curve or by calculation; and an absorbance calculating part for calculating absorbance Ac being dependent on component concentration with correction of influence by transmittance change at said triangular cell through transmitted light intensity at a time of receiving said measuring beam from said triangular cell by said linear sensor, known incident light intensity, refractive indices of the atmosphere and said cell, and said refractive index of said sample being calculated in said refractive index calculating part.

* * * * *